United States Patent
Rasche

(10) Patent No.: US 7,529,342 B2
(45) Date of Patent: May 5, 2009

(54) DEVICE AND METHOD FOR PRODUCING IMAGES OF THE HEART

(75) Inventor: Volker Rasche, Hamburg (DE)

(73) Assignee: Koninklijke Philips Electronics N.V., Eindhoven (NL)

(*) Notice: Subject to any disclaimer, the term of this patent is extended or adjusted under 35 U.S.C. 154(b) by 460 days.

(21) Appl. No.: 10/567,692

(22) PCT Filed: Aug. 3, 2004

(86) PCT No.: PCT/IB2004/051376
§ 371 (c)(1),
(2), (4) Date: Feb. 7, 2006

(87) PCT Pub. No.: WO2005/013827
PCT Pub. Date: Feb. 17, 2005

(65) Prior Publication Data
US 2006/0215815 A1  Sep. 28, 2006

(30) Foreign Application Priority Data
Aug. 12, 2003 (EP) .................... 03102510

(51) Int. Cl.
*A61B 6/00* (2006.01)
(52) U.S. Cl. .......................... 378/95; 600/428
(58) Field of Classification Search ........... 378/8, 378/95; 600/428
See application file for complete search history.

(56) References Cited

U.S. PATENT DOCUMENTS
2003/0069499 A1  4/2003  Laurent et al.

FOREIGN PATENT DOCUMENTS
DE  4210121 C1  4/1993
DE  4210122 C1  4/1993
EP  1 086 652 A1  3/2001

OTHER PUBLICATIONS
Translation of Horbascheck (DE 4210121) which was published on Apr. 29, 1993.*

* cited by examiner

Primary Examiner—Chih-Cheng G Kao

(57) ABSTRACT

The invention relates to a device and a method for producing an image of the heart (5), in which the image is preferably three-dimensional and is reconstructed from a series of X-ray projection pictures from various projection directions. In this connection, the electrocardiogram (7) is recorded in parallel with the X-ray pictures and used by a data processing device (10) to control the picture-taking rate, the X-ray pulse duration, the tube current and/or the tube voltage of the X-ray device (1) in such a way that, during the phase to be displayed of maximum movement of the heart, the mean X-ray exposure rate is higher than during the other phases. The data processing device (10) may furthermore use the electrocardiogram to drive an injection pump (8) for the contrast agent in such a way that an approximately constant contrast display of the vessels is produced with minimum contrast-agent injection despite a variable flowrate in the vascular system.

8 Claims, 1 Drawing Sheet

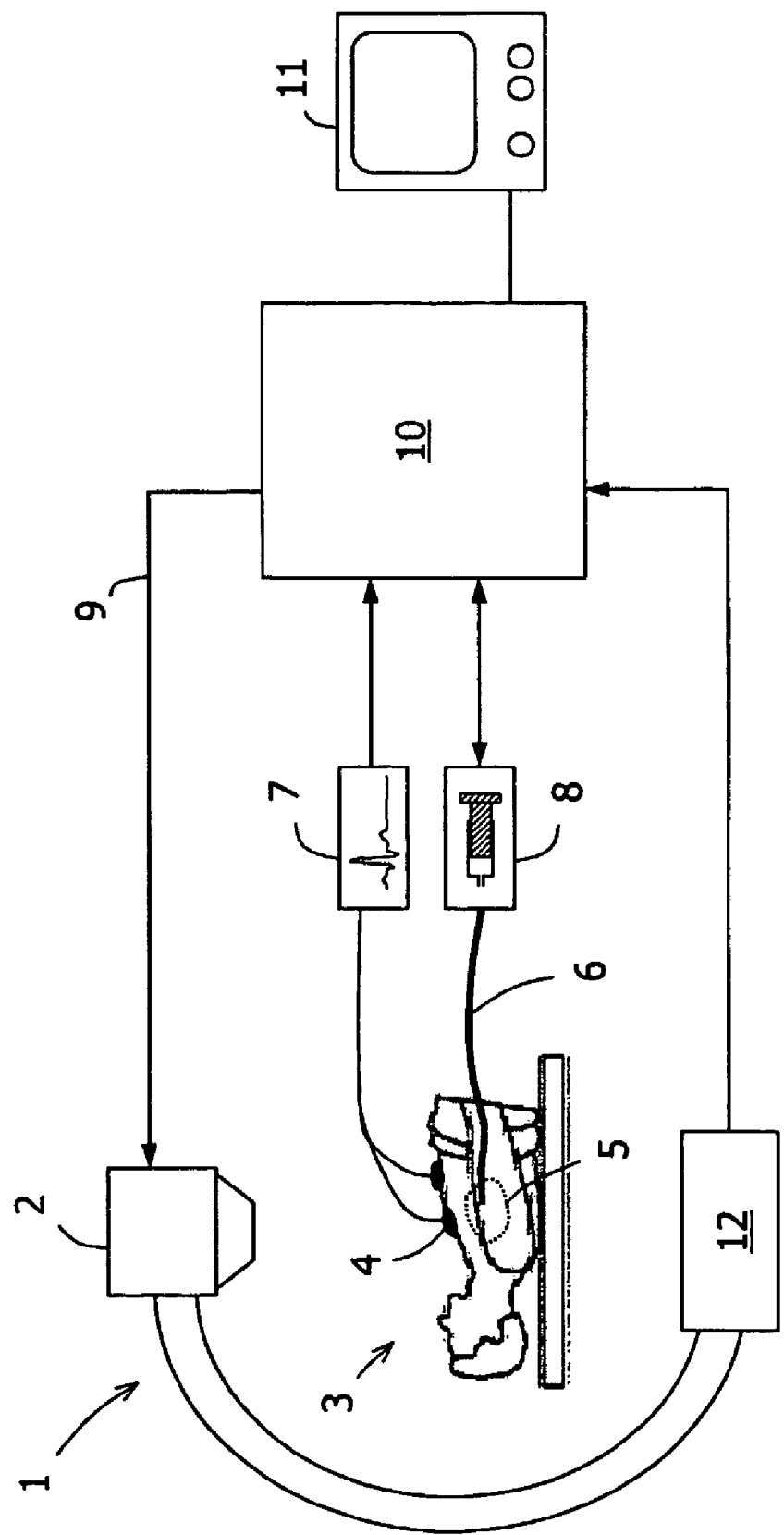

DEVICE AND METHOD FOR PRODUCING IMAGES OF THE HEART

The invention relates to a device and a method for producing images, preferably three-dimensional, of an object, in particular the heart. Furthermore, it relates to a device and a method for controlling the injection rate of a contrast agent into a vascular system.

EP 1 086 652 A1 discloses a method for producing a three-dimensional image of the coronary vessels with the aid of a rotating X-ray unit, in which the image is reconstructed from two-dimensional X-ray projections from various directions. To improve the display of the vessels, a contrast agent is generally injected during picture taking. Since, because of the heartbeat, the heart is subject to a cyclic spontaneous movement, the electrocardiogram is also recorded in the method in parallel with the X-ray pictures and is used to reconstruct only those projections that originate from the low-movement phase of the heart, the diastole. On the other hand, X-ray pictures taken during the systole are either not utilized or not even produced at all.

For many medical problems, however, three-dimensional images of the heart or of the coronary vessels are necessary during the contraction and the subsequent relaxation, that is to say the systole. If these images are to be produced with a rotating X-ray device, the highest possible picture-taking rates must be established there so that the movement phase of interest is recorded with adequate temporal and spatial resolution. A disadvantage of this is that this is associated with a high radiation exposure for the patient and the medical staff.

Against this background, it was an object of the present invention to provide means that make possible a high quality, preferably three-dimensional display of the heart even during severe spontaneous movement phases with little exposure for the patient.

This object is achieved in each case by devices and methods having the features of the advantageous embodiments disclosed herein.

In accordance with a first aspect of the invention, this relates to a device for producing a (preferably three-dimensional) image of an object that is subject to cyclical spontaneous movement. The object may, in particular, be the heart of a patient, but the invention is not restricted to this application. The device comprises the following components:

a) An X-ray unit for producing a series of two-dimensional projection pictures of the object of interest. The X-ray unit may, in particular, be a rotating X-ray unit, such as is known in computer tomography and with which projection pictures can be produced from various projection directions. As is adequately known, in addition, from the prior art, three-dimensional images of an object can be reconstructed from two-dimensional projection pictures from different directions.

b) (At least) one measuring device for determining a parameter that is characteristic of the spontaneous movement of the object observed so that the movement state of the object can be indicated by said parameter. If the object to be displayed is, for example, the heart, the measuring device may be an electrocardiograph apparatus with which an electrocardiogram can be recorded. Another example of a measuring device is a respiration sensor that delivers a signal indicating the particular respiration cycle of a patient.

c) A data processing device that is coupled to the X-ray unit and the measuring device and that is designed to drive the X-ray unit as a function of the value respectively existing of the characteristic parameter determined by the measuring device in such a way that the picture of the object is produced during a predetermined movement phase in which it is to be imaged with a higher X-ray dosage power and/or with a higher picture-taking rate than during the remaining movement phases. In particular, the data processing device may be designed in this connection to adjust the picture-taking rate, the pulse length of the one or more X-ray pulses produced for a picture, the X-ray tube current and/or the X-ray tube voltage of the X-ray unit.

Using the image-producing device described, it is possible, in particular, to reconstruct three-dimensional images of a moving object, such as, for example, the heart, even for severe spontaneous movement phases and, at the same time, to reduce the exposure for the patient and the staff to a required minimum. This is achieved by a varying adjustment of the mean X-ray exposure rate that is determined by the instantaneous X-ray exposure rate and the picture-taking rate, the variation being controlled by means of a signal characterizing the movement state of the object.

As has already been mentioned, the object displayed with the image-producing device may, in particular, be a heart that is to be displayed during the systole of the heart cycle, that is to say the time period of the contraction and the relaxation. This corresponds to the maximum spontaneous movement phase of the heart, during which a maximum picture-taking rate is necessary. The advantage of the device described is that the picture-taking rate, the X-ray pulse length, the tube current and/or the tube voltage are/is reduced to a low value during the low-movement phase of the heart.

In accordance with a second aspect, the invention relates to a device for controlling the injection rate of a contrast agent into a vascular system, such as, for instance, the coronary vessels. The device comprises the following components:

a) An injection pump for injecting the contrast agent at a controllable injection rate, wherein the injection rate can be expressed, for example, by the instantaneous volumetric or mass flow of the contrast agent.

b) A measuring device for determining a parameter characteristic of the flowrate in the vascular system (stated more precisely, at an observed point in the vascular system), wherein the flowrate in the vascular system can be expressed, in particular, by the volumetric or mass flow of the blood flowing in the vascular system. The measuring device may, for example, be an electrocardiograph apparatus that records an electrocardiogram of the electrical heart activity. Since the heartbeat drives the blood flow in the vascular system, the flow conditions in the vascular system, in particular in the region of the coronary vessels, can be inferred (approximately) from the particular heartbeat phase.

c) A control unit that is coupled to the injection pump and the measuring device and that is designed to drive the injection pump as a function of the particular value of the characteristic parameter determined with the measuring device in such a way that the contrast agent follows a predetermined concentration pattern in the vascular system.

With this device described, it is possible to match the injection rate of a contrast agent optimally to the instantaneous flow conditions in the vascular system. In known devices for injecting a contrast agent, a predetermined amount of contrast agent is injected at an approximately constant rate. Since, however, the strength of the blood flow generally alters during the duration of the injection, the injected contrast agent is distributed or carried off at different speeds. In conventional devices, the injection rate has therefore to be set high enough for the minimum contrast-agent concentration necessary for the X-ray picture to still be maintained even during the highest blood flow that occurs. During the other flow phases, however, a greater amount of contrast agent than necessary is then inevitably injected, which is a corresponding strain on the patient. These problems are avoided with the device defined above since the injection rate of the contrast agent and, consequently, the total amount of contrast agent injected is limited to a necessary minimum, the minimum being defined by the predetermined concentration pattern. Said concentration pattern may be specified, in particular, in such a way that it produces an approximately constant contrast display of the vascular system while a picture is being taken of it by an imaging device during the duration of the contrast-agent injection. In particular, the concentration pattern may be constant with time.

The invention furthermore relates to a device for producing a preferably three-dimensional image of the heart that comprises a device in accordance with the first aspect for imaging an object and also a device in accordance with the second aspect for controlling the injection rate of a contrast agent into the vascular system of the heart. In detail, the device consequently comprises the following components:

a) an X-ray unit for producing projected pictures;
b) a first measuring device for determining a parameter characteristic of the spontaneous movement of the heart;
c) a second measuring device for determining a parameter characteristic of the flowrate in the vascular system of the heart, wherein the first and the second measuring device or the associated parameters can be implemented, in particular, identically and, for example, by an electrocardiograph apparatus;
d) a data processing device for controlling the X-ray unit so that a higher X-ray exposure rate is applied during the movement phase, to be displayed, of the heart (by adapting the X-ray pulse duration, the tube current and/or the tube voltage) and/or picture-taking rate than during the other phases;
e) an injection pump for injecting a contrast agent into the coronary vessels;
f) a control unit for driving the injection rate as a function of the flowrate in the vascular system so that a predetermined concentration pattern of the contrast agent is followed. In this connection, the control unit may be identical, in particular, to the data processing unit mentioned under d).

The above-defined device has the advantage that it makes possible an imaging of the heart or of the coronary vessels with high precision, the exposure of the patient to X-ray radiation and contrast agent being simultaneously reduced to a necessary minimum.

The invention furthermore relates to a method of producing an image (for example two-dimensional or, preferably, three-dimensional) of an object that is subject to a cyclic spontaneous movement, comprising the steps of a) producing a series of projected X-ray pictures of an object; in this connection, the pictures may optionally be produced from various projection directions and used to reconstruct a three-dimensional image;
b) measuring a parameter characteristic of the spontaneous movement of the object;
c) control of the X-ray exposure rate and/or the picture-taking rate as a function of the particular value of the characteristic parameter in such a way that the X-ray exposure rate and/or the picture-taking rate is higher during a predetermined movement phase, to be displayed, of the object than during the other movement phases of the object.

Furthermore, the invention relates to a method of controlling the injection rate of a contrast agent into a vascular system comprising the steps of a) measuring the current flowrate in the vascular system;
b) injecting the contrast agent as a function of the measured flowrate at an injection rate that is such that the contrast agent in the vascular system follows a predetermined concentration pattern.

Finally, the invention relates to a method of producing an image of the heart that comprises the injection of a contrast agent and also the production of an image of the heart during the contrast-agent injection in accordance with the two methods described above.

The method relates in general form to the method steps that can be performed with the devices explained above. For a detailed description of the implementation, the advantages and the design variants of the method, reference is therefore made to the corresponding description of the devices.

These and other aspects of the invention are apparent from and will be elucidated with reference to the embodiments described hereinafter.

The sole FIGURE shows diagrammatically the components of a device according to the invention for the reconstruction of a three-dimensional image of the heart during the systole.

The left-hand part of the FIGURE shows diagrammatically a rotating X-ray unit 1 that comprises an X-ray radiation source 2 and an X-ray detector 12 that are disposed at opposite ends of a C-shaped arm. The X-ray unit 1 can be rotated around a patient 3 in a way known from computer tomography in order to produce projected two-dimensional pictures, for example, of the heart 5 of the patient 3 from various projection directions in doing so. The projections thus obtained are passed to a data processing device 10 (for example a workstation) and combined there using known methods of image processing to form a three-dimensional image of the heart or of the coronary vessels. The image reconstructed in this way can finally be displayed on a monitor 11 for the attending physician.

Since the heart 5 is subject to a strong spontaneous movement as a result of the heartbeat, only projection pictures from the same movement phase of the heart 5 can be used for the reconstruction of a three-dimensional image having acceptable quality. In order to be able to dispose the X-ray projections of a particular heart phase, an electrocardiogram is recorded simultaneously during X-raying by means of electrodes 4 and an electrocardiograph apparatus 7 and passed to the data processing device 10.

If a display of the heart 5 is required during its contraction and relaxation, that is to say the phase of greatest movement (systole), X-ray projections are produced at maximum picture-taking rate to achieve an adequate image quality and adequate resolution with time. In that case, the picture-taking rate is typically in the range from 10 to 100 X-ray projections per second. If such a rate is maintained during the entire picture series, it is associated with a correspondingly high X-ray exposure for the patient and also the medical staff.

To reduce the above-described radiation exposure to a minimum, the data processing device 10 is designed—for example, by equipment with suitable software—to drive the X-ray tube 2 (via drive signal line 9) as a function of the pattern of the measured electrocardiogram in such a way that the picture-taking rate and/or the X-ray exposure rate assume/ assumes the necessary maximum value during the movement phases to be recorded (systole), whereas it is correspondingly lower during the other movement phases (diastole). Preferably, the picture-taking rate, the X-ray pulse duration, the X-ray tube current and/or the X-ray tube voltage are/is modified by the data processing device 10 as a function of the measured electrocardiogram. Thus, for example, the picture-taking rate can be a maximum during the contraction and relaxation phase of interest for the myocardium and can be correspondingly reduced during the quiescent phase of the heart. In the extreme case, the picture-taking rate is zero during the quiescent phase of the heart and very high or a maximum during a narrow time window that should be chosen to be large enough to detect variations in the heart rate. In addition or alternatively (i.e. if the picture-taking rate is kept constant during the heart cycle), the X-ray dose applied per picture can also be reduced during the low heart-movement phase. Since more projections from these phases can be used for the reconstruction of the three-dimensional image, the picture quality does not suffer due to this reduction in dose.

The X-ray pictures explained above of the heart 5 are normally executed with simultaneous injection of a contrast agent via a catheter 6 so that the coronary vessels stand out sufficiently well against the background. In this connection, the contrast agent is injected by an injection pump 8 that can be driven, in accordance with the FIGURE, by the data processing device 10 to set a required injection rate. This drive is performed by the data processing device 10 preferably as a function of the measured electrocardiogram in such a way that the contrast agent results in an approximately constant contrast display of the coronary vessels during the entire heart cycle. In this connection, the contrast display depends on the particular concentration of the contrast agent and the latter depends in turn on the flowrate or flow speed of the blood in the vessel at the point of injection. The flowrate of the blood can be inferred at least approximately from the electrocardiogram so that the data processing device 10 is capable of executing the desired matched control of the contrast agent injection. Such a variable contrast-agent injection has the important advantage that the patient is stressed to a minimum by the contrast agent.

The invention claimed is:

1. A device for producing images of an object that is subject to a cyclic spontaneous movement and for controlling an injection rate of a contrast agent in a vascular system of the object, comprising:
   a) an X-ray unit for producing a series of two-dimensional projected pictures of the object;
   b) a measuring device for determining a parameter characteristic of the spontaneous movement of the object;
   c) a data processing device that is coupled to the X-ray unit and the measuring device and that is designed to drive the X-ray unit as a function of a particular value of the spontaneous movement characteristic parameter in such a way that, during a predetermined movement phase to be displayed corresponding to a movement phase of greatest movement, pictures are taken of the object with a higher X-ray exposure rate and/or picture-taking rate than during the other movement phases;
   d) an injection pump for injecting the contrast agent at a controllable injection rate;
   e) a measuring device for determining a parameter characteristic of a flowrate in the vascular system; and
   f) a control unit that is coupled to the injection pump and the flowrate parameter characteristic measuring device, the control unit configured to drive the injection pump as a function of a particular value of the parameter characteristic of the flowrate in such a way that (i) the contrast agent follows a predetermined concentration pattern in the vascular system, (ii) the injection rate of the contrast agent is matched to instantaneous flow conditions in the vascular system, and (iii) a total amount of contrast agent injected is limited to a necessary minimum, the necessary minimum being defined by the predetermined concentration pattern, the predetermined concentration pattern further being specified to produce a constant contrast display of the vascular system while pictures are being taken of the object during a duration of the contrast agent injection.

2. A device as claimed in claim 1, characterized in that the data processing device is designed to adjust the picture-taking rate, X-ray pulse duration, tube current and/or tube voltage of the X-ray unit.

3. A device as claimed in claim 1, characterized in that the object is a heart.

4. A device as claimed in claim 1, characterized in that the spontaneous movement characteristic parameter measuring device is an electrocardiograph apparatus.

5. A method of producing an image of an object that is subject to cyclic spontaneous movement and for controlling an injection rate of a contrast agent in a vascular system of the object, the method comprising:
   a) producing a series of projected X-ray pictures of the object;
   b) measuring a parameter characteristic of the spontaneous movement of the object;
   c) controlling an X-ray exposure rate and/or a picture-taking rate as a function of a particular value of the spontaneous movement characteristic parameter in such a way that the X-ray exposure rate and/or the picture-taking rate is higher during a predetermined movement phase, to be displayed corresponding to a movement phase of greatest movement of the object than during the other movement phases of the object;
   d) injecting the contrast agent at a controllable injection rate with an injection pump;
   e) measuring a parameter characteristic of a flowrate in the vascular system; and
   f) controlling the injection pump as a function of a particular value of the parameter characteristic of the flowrate in such a way that (i) the contrast agent follows a predetermined concentration pattern in the vascular system, (ii) the injection rate of the contrast agent is matched to instantaneous flow conditions in the vascular system, and (iii) a total amount of contrast agent injected is limited to a necessary minimum, the necessary minimum being defined by the predetermined concentration pattern, the predetermined concentration pattern further being specified to produce a constant contrast display of the vascular system while pictures are being taken of the object during a duration of the contrast agent injection.

6. The method of claim 5, characterized in that controlling the X-ray exposure rate and/or picture-taking rate comprises adjusting the picture-taking rate, X-ray pulse duration, tube current and/or tube voltage of an X-ray unit configured to implement the method.

7. The method of claim 5, characterized in that the object is a heart.

8. The method of claim 5, characterized in that the spontaneous movement characteristic parameter is an electrocardiograph measurement.

* * * * *